United States Patent [19]

Denny et al.

[11] Patent Number: 4,946,660

[45] Date of Patent: Aug. 7, 1990

[54] DESULPHURIZATION

[75] Inventors: Patrick J. Denny, Darlington; David G. Shipley, Stockton-on-Tees, both of Great Britain

[73] Assignee: Imperial Chemical Industries PLC, London, England

[21] Appl. No.: 317,569

[22] Filed: Mar. 1, 1989

[30] Foreign Application Priority Data

Mar. 7, 1988 [GB] United Kingdom ................. 8805351

[51] Int. Cl.$^5$ ...................... C01B 17/16; C01B 31/20; C02F 1/68; B01J 38/48
[52] U.S. Cl. .................................... 423/230; 210/749; 210/751; 502/22; 502/38; 502/55; 502/400; 502/517
[58] Field of Search ................ 423/230; 210/749, 751; 502/38, 22, 55, 400, 517

[56] References Cited

U.S. PATENT DOCUMENTS

| | | | |
|---|---|---|---|
| 3,441,370 | 4/1969 | Gutmann et al. | 23/2 |
| 4,425,312 | 1/1984 | Brigna | 423/230 |
| 4,442,078 | 4/1984 | Jalan et al. | 423/230 |
| 4,533,529 | 8/1985 | Lee | 423/230 |
| 4,842,843 | 6/1989 | Pendergraft | 423/230 |

FOREIGN PATENT DOCUMENTS

| | | |
|---|---|---|
| 0230146 | 7/1987 | European Pat. Off. . |
| 2650711 | 10/1977 | Fed. Rep. of Germany ...... 423/230 |

*Primary Examiner*—Robert L. Stoll
*Assistant Examiner*—Lori F. Cuomo
*Attorney, Agent, or Firm*—Cushman, Darby & Cushman

[57] ABSTRACT

Low temperature desulphurization process using a bed of zinc oxide-containing absorbent in which the water content within the bed is temporarily increased, thereby increasing the sulphur absorption capacity of the absorbent.

10 Claims, No Drawings

DESULPHURIZATION

This invention relates to desulphurisation and in particular to the removal of sulphur compounds such as hydrogen sulphide from a gaseous or liquid feedstock stream, particularly hydrocarbon feedstock streams such as natural gas. Such hydrocarbon feedstock streams often contain substantial amounts of sulphur compounds, for example, where the hydrocarbon is gaseous, in an excess of 50 ppm by volume expressed as equivalent hydrogen sulphide.

Desulphurisation of a gaseous or liquid feedstock stream can be affected by passing the feedstock stream through a suitable absorbent such as zinc oxide in the form of a bed or beds of granules or pellets, wherein the absorbent combines with that sulphur present so as to form a sulphided absorbent, for example zinc sulphide in the case of a zinc oxide absorbent.

While such beds of absorbent enable a product stream of low sulphur content, typically below 10 ppm, to be obtained, breakthrough of the sulphur compounds into the product stream generally occurs long before all of the absorbent is fully sulphided.

Premature breakthrough is particularly noticeable where the absorption temperature is low.

Although absorbents having a high surface area, typically above 20, and particularly in the range 50 to 200, $m^2.g^{-1}$ are of particular use for low temperature desulphurisation of gaseous or liquid feedstock streams, e.g. at temperatures between $-10°$ and $200°$ C., they are still susceptible to the problem of premature breakthrough.

By the term breakthrough we mean that the sulphur content of the product stream is at a level that is unacceptable to the user. This level will of course depend on the use to which the product stream is to be put.

By the term absorption capacity, when used with reference to a sulphur absorbent, we mean the amount of sulphur retained by the absorbent before breakthrough occurs.

By the term regeneration, when used with reference to a sulphur absorbent, we mean the increasing of the absorption capacity of a sulphur absorbent without removal of sulphur from the absorbent.

It has been proposed in GB-A-1568703 to adjust the water vapour content of a synthesis gas stream, i.e. a gas stream containing hydrogen and carbon oxides, to 0.5 to 5% by volume prior to desulphurisation with a zinc oxide bed. In this reference the desulphurisation is preferably effected at temperatures above $200°$ C. The object of incorporation of water vapour in the gas stream used in the process of that reference was to suppress the formation of sulphur compounds such as carbonyl sulphide and carbon disulphide which are less readily removed than hydrogen sulphide from gas streams. Such compounds presumably result from the reactions:

$$H_2S + CO_2 \rightarrow H_2O + COS \quad (1)$$

$$H_2S + COS \rightarrow H_2O + CS_2 \quad (2)$$

These reactions are reversible and so the formation of carbonyl sulphide and carbon disulphide is suppressed by the incorporation of water in the gas stream. The equilibrium constants for reaction (1) above are given for various temperatures at pages 203 and 306 of Catalyst Handbook, 2nd Edition, edited by M V Twigg, published by Wolfe Publishing Ltd. At equilibrium, the extent of reaction (1) reduces with temperature, and at low temperatures the extent of reaction is negligible. Furthermore, the rates of reaction for reactions (1) and (2) are believed to be also very small at low temperatures and so carbonyl sulphide and carbon disulphide formation is unlikely to be a problem when effecting desulphurisation of carbon dioxide-containing feedstock streams at low temperatures.

It has been further proposed in EP-A-279116 that the continued presence of a controlled amount of water in the feedstock stream, particularly a gaseous feedstock stream, such that the relative humidity of the water in the feedstock stream is above 30%, has the effect of increasing the absorption capacity of zinc oxide containing absorbent beds when operating at low temperatures.

However, in a number of applications, the continued presence of water is not desirable and consequently the option of continuously adding water to improve the sulphur absorption capacity of the absorbent is not acceptable. For instance, when in contact with substantial quantities of water at relatively low temperatures, methane may give rise to the formation of methane hydrates, which are prone to cause blockages and operating difficulties; therefore it is not desirable to generate a low temperature methane-containing stream which also contains a high level of water on a continuous basis.

We have found that the absorption capacity of certain zinc oxide containing absorbents can be usefully increased if the proportion of water in the feedstock or other fluid stream passing or otherwise making contact with the absorbent is temporarily increased. Thus a bed of zinc oxide-containing absorbent may be regenerated by such treatment and the useful life of the absorbent extended.

Accordingly the present invention provides a process for the removal of hydrogen sulphide from a substantially water-free hydrogen sulphide-containing feedstock stream comprising passing the feedstock stream, at a temperature between $-10°$ and $350°$ C. through a bed of zinc oxide-containing absorbent particles thereby forming a hydrogen sulphide-depleted product stream characterised in that, in order to increase the absorption capacity of the particles for hydrogen sulphide, after a period of use for absorption of hydrogen sulphide from the feedstock stream, the particles are contacted with a water-containing fluid so as to temporarily increase the water content within the fluid space of the bed for a period of time until the particles absorb such an amount of water that the particles increase in weight by an amount in the range 0.5 to 20%.

Although a slight increase in the absorption capacity of the absorbent particle may be seen after the absorbent particles have absorbed smaller amounts of water, significant increases are only obtained if the particles absorb at least 0.5% by weight of water. However, the amount of water employed is preferably such as to increase the weight of the particulate sulphided absorbent by between 1.5 to 10%, and particularly between 2 to 8%. The amount of water required depends to some extent on the surface area of the absorbent: thus more water is required for high surface area absorbents than with low surface area absorbents. It is preferred that the amount of water employed is such that the absorbent absorbs at least 0.2 mg, and preferably at least 0.5 mg, of water per $m^2$ of absorbent surface area.

The treatment of the particles by temporarily increasing the water content within the fluid space of the bed constitutes regeneration of the absorbent.

The bed of zinc oxide-containing absorbent particles may be subjected to the regeneration whilst absorbing sulphur compounds from the feedstock stream if the resultant increase in water content of the product stream is acceptable. Alternatively, and in some cases preferably, the bed is regenerated whilst the bed is not absorbing sulphur compounds from the feedstock stream. Thus in a continuous process for the generation of a product stream, two or more beds of absorbent may be provided and, while one or more beds are removing sulphur compounds from the feedstock stream, one or more other beds are subjected to regeneration.

The regeneration may be effected by the continuous flow of a water-containing fluid, i.e. either a gas or liquid, through the absorbent bed, or the holding of such a water-containing fluid within the bed for the required period.

The water-containing fluid used to effect the regeneration may be any water-containing fluid stream which does not adversely affect the desulphurisation properties of the absorbent. In some cases it may be possible to employ a feedstock stream to which water has been added as the water-containing fluid: in this case, of course, absorption of the sulphur compounds will continue during contact of the water-containing stream with the bed of absorbent, so the absorbent should be regenerated sufficiently before breakthrough of sulphur compounds into the product stream occurs.

Alternatively the water-containing fluid used to effect regeneration may be part of the product stream to which water has been added. After use for regeneration, the part stream may be returned to the remainder of the product stream. Where the presence of water in the product stream is not acceptable, the part stream may be dried, for example by the use of a molecular sieve, before return to the remainder of the product stream, or the whole of the product stream may be dried after return of the part stream. Indeed, since the absorption of hydrogen sulphide by zinc oxide produces water, it may in some cases be necessary to dry the product stream before further use. In this case it is convenient that a part of the product stream is taken before the drier, water is added, and the water-laden part product stream is used as the water-containing fluid for regeneration. After use for regeneration, this water-laden part product stream is returned to the remainder of the product stream and when the whole of the product stream is passed through the drier, e.g. a molecular sieve.

Where the regeneration is effected by means of a water-containing gas, it is preferred that the water-containing gas is passed through the bed of absorbent continuously during the regeneration stage.

Where such a water-containing gas is to be used to effect the regeneration, provision may be made for heating the gas prior to addition of the water, so that the quantity of water held as vapour per quantity of gas is increased, thereby accelerating the rate at which the increase in absorption capacity of the absorbent is achieved. The water-containing gas preferably has a relative humidity, at the regeneration temperature, of at least 25%, preferably at least 50%, and most particularly at least 75%. Where the absorbent comprises substantially only zinc oxide, the water-containing gas preferably is substantially free from carbon dioxide in order to avoid the formation of zinc carbonate which has an absorption capability for sulphur compounds inferior to that of zinc oxide.

Where the presence of liquid water in the absorbent bed and/or in the water-containing gas from the absorbent bed, is not desirable, then provision may be made for heating the water-containing gas, and/or the vessel in which the absorbent is held, so that the water-containing gas as it both enters and leaves the bed is free of liquid water.

In one application of the invention the desulphurisation stage is operated in combination with a drying stage employing a molecular sieve drier which is regenerated by passage of a heated fluid stream therethrough to effect desorption of the water removed during the drying stage. In such a process, in some cases it may be possible to employ the water-containing fluid leaving the molecular sieve during the regeneration thereof as the water-containing fluid used to effect regeneration of the zinc oxide containing absorbent.

Where the regeneration of the zinc oxide containing particles is effected with a water-containing liquid, it is preferred that an appropriate amount of water-containing liquid is charged to the bed, (and an excess of such liquid may be employed), the bed held in that state until the absorbent has absorbed the requisite amount of water, and then the bed is freed of liquid water by passage of a dry gas or liquid stream therethrough. The amount of such a water-containing liquid, which is preferably water substantially free from any other materials, is preferably sufficient to fill the pores of the absorbent.

Where a water-containing liquid is used to effect the regeneration provision may be made for heating the water-containing liquid, and/or the vessel in which the absorbent is held, thereby accelerating the rate at which the increase in absorption capacity of the absorbent is achieved.

Contacting the water-containing fluid with the absorbent for the required length of time enables the absorbent to absorb the required amount of water for regeneration. Once regenerated the absorbent may again be used to remove sulphur compounds from the feedstock stream. However the initial contact of the feedstock stream with the absorbent after regeneration of the absorbent will tend to strip-off that water which has been absorbed by the absorbent. The water which has been stripped-off will be carried through the bed of absorbent to emerge in the product stream. The water content in the product stream will therefore initially increase, and then drop back as the amount of water which is stripped-off diminishes. Where the initial increase in the water content of the product stream can be tolerated, for instance where the product stream would in any event be dried, this may not present a problem. However in some cases an initial increase in the water content of the product stream, after regeneration of the absorbent may be a problem. In such cases the absorbent may be dried before the feedstock stream is reintroduced to the bed. The drying of the absorbent may be achieved in a number of ways, for example by passage of a dry inert stream through the bed, or by passage of a fluid stream that is subsequently to be used as the water-containing fluid for regenerating another bed of absorbent.

The time interval required before the regeneration will depend on the rate at which the absorbent becomes sulphided, e.g. upon the nature and proportions of the absorbable sulphur compounds in the feedstock stream, the space velocity at which the feedstock stream is fed through the bed, on the nature of the feedstock stream, the temperature at which the absorption takes place, and the acceptable level of sulphur compounds in the effluent product stream.

The particulate absorbent material preferably comprises at least 60%, especially at least 80%, by weight of zinc oxide, calculated on the constituents of the absorbent material non-volatile at 900° C. As used in the process the zinc oxide may be, at least initially, wholly or partly hydrated or in the form of a salt of a weak acid, e.g. a carbonate.

The absorbent is preferably particulate in form, particularly in the form of porous agglomerates, as may be made, for example, by mixing a finely divided zinc oxide composition with a cement binder and a little water, insufficient to give a slurry, and then granulated or extruded. In order to aid access of the feedstock stream into the particulate absorbent, the latter may be provided in the form of extruded pellets having a plurality of through passages.

It is believed that the absorption efficiency and hence the life of a particulate zinc oxide-containing absorbent depends on the rate of diffusion of that sulphur which has been absorbed by the zinc oxide present on the surface of the absorbent, away from the surface of the absorbent. As the rate of adsorption of sulphur compounds at low absorption temperatures is controlled by the exposed zinc oxide surface area, it is preferable when operating at absorption temperatures below 120° C., preferably below 80° C., and particularly below 50° C., to employ a particulate zinc oxide-containing absorbent having a high pore volume, above 0.2 cm$^3$.g$^{-1}$, and high surface area, above 50 m$^2$.g$^{-1}$, preferably in the range 70 to 200 m$^2$.g$^{-1}$. With a particulate zinc oxide-containing absorbent having a lower pore volume and a surface area of the order of 25 to 30 m$^2$.g$^{-1}$, the increase in absorption capacity by the temporarily rise in the water content of the fluid space is not nearly so significant and so the useful life of such a low surface area absorbent at low absorption temperatures is relatively low. Thus large volumes of low surface area absorbent would be needed in order to avoid premature breakthrough of the sulphur compounds into the product stream. However, by using a zinc oxide-containing absorbent of pore volume above, for example, 0.25 cm$^3$.g$^{-1}$ and surface area above, for example, 70 m$^2$.g$^{-1}$, the volume of absorbent required can be markedly reduced, e.g. to about one third of that required with a low surface area absorbent. The particulate zinc oxide-containing absorbents employed thus preferably have a surface area above 70 m$^2$.g$^{-1}$ and a pore volume above 0.25 cm$^3$.g$^{-1}$.

Preferred particulate absorbents for the process at low absorption temperatures have a hydrogen sulphide absorption capacity of at least 20%, especially at least 25%, of the theoretical maximum, at a temperature of 25° C., as determined in a standard test in which a dry mixture of hydrogen sulphide (2000 ppm by volume), carbon dioxide (4% by volume), and methane (balance) is passed through a bed of the particulate absorbent at atmospheric pressure and a space velocity of 700 h$^{-1}$ using a bed of circular cross section having a length to diameter ratio of 5.

A particularly suitable particulate zinc oxide containing absorbent is that sold by Imperial Chemical Industries plc as "Catalyst 75-1". This absorbent is in the form of granules typically having a surface area of the order of 80 m$^2$.g$^{-1}$ and a pore volume of about 0.3 cm$^3$.g$^{-1}$, and an adsorption capacity of about 27% of theoretical when measured by the above procedure.

Alternatively the particulate absorbent may comprise agglomerates of particles of an intimate mixture of oxides, hydroxides, carbonates and/or basic carbonates of copper, and zinc and/or at least one element such as aluminium as described in EP-A-243052.

Water-free gaseous feedstocks that may be treated are those that are less than 10%, and especially less than 1%, saturated with water.

Alternatively, the process of the present invention may be used to treat liquid substantially water-free feedstock streams wherein the amount of water (if any) in the feedstock stream is insufficient to fill the pores of the absorbent.

The feedstock stream typically contains hydrocarbons up to those containing six carbon atoms. Usually it will contain, in addition to methane, and one or more of ethane, propane, propene, butanes, and butenes. The invention is also of utility with other feedstocks, for example air, naphtha, carbon dioxide, or the product of fractionating a gas mixture produced by cracking or hydrocracking a normally liquid hydrocarbon feedstock, or the gaseous by-product of a zeolite-catalysed conversion of a feedstock such as methanol to gasoline.

The composition of the raw gas, where the latter is a natural or oilfield associated gas, expressed by volume, is typically:
ethane: 2 to 20 %
propane plus propene: 1 to 10 %
butanes plus butenes: 0.5 to 5 %
higher hydrocarbons: 0.2 to 2 %
carbon dioxide: 0 to 20 %
nitrogen: 0 to 20 %
water: up to saturation
methane: balance.

When such natural or oilfield associated gas streams contain substantial amounts of water, i.e. the stream is above 10% saturated, a drying stage is normally employed to reduce the amount of water present prior to sulphur removal. The dried stream is then desulphurised. The use of the present invention in the desulphurisation of such streams enables the absorption capacity of the absorbent to be increased without reintroducing significant amounts of water into the stream.

In addition to hydrogen sulphide, other sulphur containing compounds that are initially present in the feedstock stream may be removed by the process of the present invention. Examples of such compounds include carbonyl sulphide, carbon disulphide, methyl, ethyl or other mercaptans, diethyl sulphide and other alkyl sulphides up to $C_{10}$, and/or tetrahydrothiophene. The total initial concentration of sulphur compounds, expressed as sulphur equivalent hydrogen sulphide, is typically in the range 1 to 1000 ppm by volume of the feedstock when the latter is in the gaseous phase. The absorption stage can be conducted so that a substantial proportion, e.g. over 75% by volume of the sulphur content of the feedstock stream can be removed. Typically the sulphur compounds content of the product stream is under 10, for example under 5, ppm by volume, expressed as above, but this is a matter of design, depending on the user's requirements.

Without wishing to be limited it is thought that a possible explanation of the increase in absorption capacity of a bed of particulate zinc oxide-containing absorbent, resulting from the temporary increase in the amount of water in the fluid space of the bed, is that the reaction mechanism for the absorption of hydrogen sulphide by zinc oxide, particularly at low temperatures, may involve the hydration of the zinc oxide surface, indicated in a simplistic form by the following equations $$ZnO + H_2O \rightarrow Zn(OH)_2$$

$$Zn(OH)_2 + H_2S \rightarrow ZnS + 2H_2O$$

$$Zn(OH)_2 + 2H_2S \rightarrow Zn(SH)_2 + 2H_2O$$

in preference to the reaction $$ZnO + H_2S \rightarrow ZnS + H_2O$$

which is the prevalent mechanism at high temperatures and which proceeds only slowly at low temperatures. The surface hydrated zinc oxide provides mobile hydroxy or SH (bisulphide) groups that allow the movement of sulphur away from the sulphur saturated exterior thereby generating new sulphur deficient absorbent on the surface.

The invention is illustrated by the following examples. In these examples about 60 ml of the absorbent in the form of granules were charged to a tube of internal diameter 2.54 cm to form a vertical bed of length 12 cm.

The sulphur absorption capacity of the bed of absorbent was tested, in an absorption stage, by passing a test gas substantially at atmospheric pressure, down through the bed maintained at about 20° C. at a rate of 700 ml/min, (i.e. space velocity 700 $hr^{-1}$).

The test gas was "dry" methane (which contained about 120 ppm by volume of water) in admixture with about 1% by volume of hydrogen sulphide.

The hydrogen sulphide content of the test gas leaving the bed of absorbent was monitored and breakthrough was deemed to have occurred when the hydrogen sulphide content of the test gas exit the bed of absorbent reached about 2 ppm by volume.

The absorbent was then regenerated as described in the individual examples.

After regeneration, the flow of test gas was resumed and the time taken for breakthrough to reoccur was measured.

At the conclusion of each experiment the absorbent was discharged in six equal parts A to F, (A=top; F=bottom) which were analysed so that the distribution of sulphur down the depth of the bed could be determined.

EXAMPLE 1

This example shows the effect on the absorption capacity of an absorbent with repeated regeneration using a water-containing gas.

The absorbent employed was granules of size approximately 3 to 5 mm of ICI "Catalyst 75-1".

The water-containing gas used to regenerate the absorbent, in a regeneration stage, was "wet" hydrogen sulphide-free methane, obtained by saturating the "dry" methane with water at 20° C. The "wet" methane was passed down through the bed of absorbent at about 20° C. and substantially at atmospheric pressure at a space velocity of 700 $hr^{-1}$.

As a comparative experiment, a similar bed of absorbent was regenerated by passing "dry" hydrogen sulphide-free methane substantially at atmospheric pressure, down through the bed of absorbent maintained at about 20° C. at a space velocity of 700 $hr^{-1}$.

The absorbent regenerated according to the present invention was then subjected to a succession of absorption and regeneration stages.

The results are shown in the following table in which an absorption stage and the regeneration stage immediately following are termed a "cycle"; $T_{BTR}$ is the time to breakthrough from the start of the absorption stage; and $T_{REG}$ is the duration of the regeneration stage.

| Cycle | "Dry" regeneration gas | | "Wet" regeneration gas | |
|---|---|---|---|---|
| | $T_{BTR}$ (hours) | $T_{REG}$ (hours) | $T_{BTR}$ (hours) | $T_{REG}$ (hours) |
| First | 5.9 | 22.5 | 6.4 | 21.5 |
| Second | 0.2 | — | 1.9 | 24 |
| Third | — | — | 1.0 | 23 |
| Fourth | — | — | 1.0 | >6.5* |
| Fifth | — | — | 0.5 | 24 |
| Sixth | — | — | 0.4 | — |
| Total | 6.1 | 22.5 | 11.2 | >99 |

*Precise time not known, but less than 19 hours.

The difference between the breakthrough time for the first cycle of the comparative experiment (5.9 hr) compared with that of the present invention (6.4 hr) probably reflects differences in the precise amount of absorbent employed and/or minor variations in the hydrogen sulphide content of the test gas.

The following table shows the sulphur content down the beds of absorbent on termination of the experiment after the second cycle ("dry" gas) and sixth cycle ("wet" gas). The sulphur content down a bed of absorbent after the first cycle, i.e. without further sulphur absorption occurring, is included for additional comparison.

| | Sulphur content (% w/w) | | |
|---|---|---|---|
| | Regenerated | | Non- |
| Bed Portion | "Dry" Gas | "Wet" Gas | Regenerated |
| A | 10.3 | 18.1 | 7.9 |
| B | 10.5 | 17.2 | 8.1 |
| C | 9.9 | 15.8 | 7.9 |
| D | 7.8 | 12.2 | 5.9 |
| E | 4.1 | 7.0 | 2.0 |
| F | 1.1 | 2.2 | 0.3 |
| Average | 7.3 | 12.1 | 5.4 |

It is seen that the successive "regeneration" stages enabled the useful life of the absorbent to be increased by about 84% and thereby retaining an additional 66% more sulphur.

EXAMPLE 2

In this example the application of the invention to a zinc oxide absorbent used for desulphurising damp carbon dioxide-containing gas (wherein the absorbent becomes carbonated during use), is simulated, by repeating the procedure of Example 1 using a "carbonated" absorbent.

The "carbonated" absorbent was obtained by enclosing a sample of the fresh absorbent as employed in Example 1, with solid carbon dioxide, and water, which were in proportions of 10:1 on a weight basis in an autoclave, allowing the temperature to rise to ambient, and maintaining at ambient temperature for 48 hours. This "carbonated" absorbent was then dried for 16 hours at 110° C. before use. As in Example 1, the regeneration of the absorbent was effected using the "wet" hydrogen sulphide-free methane, and in a comparative experiment with the "dry" hydrogen sulphide-free methane. The results are shown in the following table:

| Cycle | "Dry" regeneration gas | | "Wet" regeneration gas | |
|---|---|---|---|---|
| | $T_{BTR}$ (minutes) | $T_{REG}$ (hours) | $T_{BTR}$ (minutes) | $T_{REG}$ (hours) |
| First | 21 | 23 | 25 | 24 |
| Second | 7 | — | 53 | >8.5* |
| Third | — | — | 59 | 21.5 |
| Fourth | — | — | 57 | 19.5 |
| Fifth | — | — | 50 | 23 |
| Sixth | — | — | 56 | 21.5 |
| Seventh | — | — | 55 | — |
| Total | 28 | 23 | 355 | >118 |

*Precise time not known, but less than 19 hours.

As in Example 1, the difference between the time to breakthrough for the first cycle for the comparative experiment (21 minutes) compared with that of the present invention (25 minutes) probably reflects differences in the precise amount of absorbent employed and/or minor variations in the hydrogen sulphide content of the gas.

After the second cycle ("dry" gas) and sixth cycle ("wet" gas), the sulphur content of the absorbent down the bed was as follows:

| Bed Portion | Sulphur content (% w/w) | |
|---|---|---|
| | "Dry" regeneration gas | "Wet" regeneration gas |
| A | 0.9 | 12.9 |
| B | 1.1 | 11.5 |
| C | 1.0 | 9.4 |
| D | 0.9 | 7.1 |
| E | 0.6 | 4.3 |
| F | 0.4 | 1.3 |
| Average | 0.8 | 7.8 |

It is seen, that by comparing the results of this example with those of Example 1, that the "carbonated" zinc oxide absorbent has a much inferior sulphur absorption capability to that of the uncarbonated zinc oxide absorbent used in Example 1, but the successive regeneration stages with "wet" gas enabled the useful life of the "carbonated" zinc oxide absorbent to be increased dramatically.

EXAMPLE 3

In this example the effect is shown of incorporating a drying stage after the regeneration stage of the cycle.

The procedure of Example 1 was repeated, but using only a single regeneration stage using the "wet" hydrogen sulphide-free methane.

After the regeneration stage, the absorbent was dried by passing "dry" hydrogen sulphide-free methane down through the bed of absorbent.

During the regeneration and drying stages, the weight of the absorbent was monitored in order to determine the degree of "water pickup". The "water pickup" is a measure of that water retained by the bed of absorbent and is the weight of water in the bed of absorbent after contact with the water-containing fluid, and immediately before a subsequent drying stage, divided by the total weight of absorbent and sulpher in the bed at the start of the regeneration stage.

The results are shown in the following table and indicate that the effects of the regeneration are apparent after the absorbent has been dried.

| Cycle Stage | Total time (hours) from start of Cycle Stage | Water Pickup (% w/w) |
|---|---|---|
| Regeneration | 0 | 0 |
| | 18.5 | 6.5 |
| | 19.5 | 6.6 |
| | 21.5 | 6.9 |
| | 22 | — |
| | 22.5 | 6.9 |
| Drying | 0 | 6.9 |
| | 1 | 5.8 |
| | 3 | — |
| | 4 | — |
| | 17.5 | 1.5 |
| | 19 | 1.3 |
| | 21 | — |
| | 22 | 1.2 |

| | Time to Breakthrough (minutes) |
|---|---|
| First Cycle | 349 |
| Second Cycle | 102 |

| Bed Portion | Sulphur Content (% w/w) |
|---|---|
| A | 12.5 |
| B | 12.7 |
| C | 11.8 |
| D | 9.0 |
| E | 5.5 |
| F | 2.1 |
| Average | 8.9 |

EXAMPLE 4

In this example the effect is shown of regenerating the absorbent with a water-containing liquid.

The absorbent was a sample of the fresh absorbent granules as used in Example 1.

The absorption stages were as conducted in the previous examples. The first absorption stage was terminated on breakthrough, after 4.4 hours.

The regeneration stage was then effected by adding sufficient liquid water to the bed of absorbent so as to fill the pores of the absorbent with water. The bed of absorbent was then left at ambient temperature, without flow of gas or liquid therethrough, for 16 hours. The bed of absorbent was then dried out for 22 hours to a constant weight by passing "dry" hydrogen sulphide-free methane down through the bed at a temperature of about 20° C. and at atmospheric pressure.

A second cycle was then started, and when breakthrough reoccurred after 1.4 hours, the bed was again regenerated and dried in the same manner as described above.

Flow of the test gas (i.e. "dry" methane in admixture with hydrogen sulphide) was again recommenced and the experiment was terminated on subsequent breakthrough.

The total time during which the bed of absorbent was absorbing sulphur from the test gas, without breakthrough occurring, was 7.3 hours and the sulphur content of the absorbent down the bed, on termination of the experiment, was as follows:

| Bed Portion | Sulphur Content (% w/w) |
|---|---|
| A | 16.1 |
| B | 16.1 |
| C | 14.4 |
| D | 11.4 |
| E | 6.4 |
| F | 1.6 |
| Average | 11.0 |

EXAMPLE 5

This example shows the effect of different regeneration times.

The absorbent employed was a sample of the fresh granules as employed in Example 1.

Nitrogen saturated with water at ambient temperature was used as the water-containing gas used in the regeneration stage. The regeneration stages were conducted at ambient temperature, in a manner similar to that of Example 1.

In some cases a drying stage was conducted after the regeneration stage. The drying stage comprised passing dry nitrogen down through the bed of absorbent at about ambient temperature, and atmospheric pressure, for 16 hours prior to recommencing passage of the test gas ° through the bed of absorbent.

The results are shown in the following tables.

In some cases the absorbent was subjected to more than one cycle, comprising an absorption stage and a regeneration stage. At least one drying stage was included in the multiple cycle cases.

Thus in experiment 5f the absorbent was subjected to in turn an initial absorption stage; an initial regeneration stage of 2 hours duration; a second absorption stage; a second regeneration stage of 4 hours duration; a third absorption stage; a third regeneration stage of 8 hours duration; a drying stage; a fourth absorption stage; a fourth regeneration stage of 6 hours duration; a second drying stage; and a fifth, and final, absorption stage.

| | Regeneration | | Bed portion sulphur content (% w/w) | | | | | |
|---|---|---|---|---|---|---|---|---|
| | Number | Time (h) | A | B | C | D | E | F |
| 5a | 1 | 0.50* | 10.7 | 11.1 | 10.4 | 8.2 | 4.5 | 1.3 |
| 5b | 1 | 1.17* | 11.4 | 12.0 | 11.2 | 8.6 | 4.1 | 1.0 |
| 5c | 1 | 2* | 11.9 | 12.2 | 11.9 | 10.4 | 7.0 | 3.5 |
| 5d | 1 | 4* | 12.0 | 12.2 | 11.2 | 8.8 | 4.6 | 1.2 |
| 5e | 1 | 8.* | 12.4 | 12.6 | 12.0 | 9.6 | 6.0 | 1.9 |
| 5f | 4 | 2 4 8* 6* | 17.7 | 17.2 | 15.5 | 12.2 | 7.4 | 2.6 |
| 5g | 3 | 2* 4* 8* | 14.1 | 13.8 | 13.0 | 10.7 | 6.9 | 2.5 |

| | Total Time To Breakthrough (h) | Water Pickup (% w/w) |
|---|---|---|
| 5a | 6.95 | 0.63 |
| 5b | 6.15 | 0.90 |
| 5c | 5.00 | 1.52 |
| 5d | 5.18 | 2.83 |
| 5e | 5.30 | 4.33 |
| 5f | 7.32 | — |
| 5g | 6.95 | — |

*Dried after regeneration

The "Water Pickup" is as previously defined.

The "Total Time To Breakthrough (h)" is the total time that the bed of absorbent was removing sulphur from the test gas, without breakthrough occurring. Variations in the concentration of hydrogen sulphide in the test gas during the experiments are reflected in the breakthrough times in some instances being less than that of the "dry" gas regenerated absorbent of Example 1. However the absorption capacity of the absorbent has in all instances been increased to above that of the "dry" gas regenerated absorbent of Example 1.

The concentration profile of absorbed sulphur down the bed shows a relatively sharp trailing edge, plus a small tail in the bottom third of the bed. It is the tail that determines when breakthrough occurs. However improvement in the absorption capacity can be seen by comparing the top half to two thirds of each absorbent bed.

EXAMPLE 6

In this example the effect is shown of regeneration by a water-containing gas at a temperature higher than 20° C.

The absorbent employed was a sample of fresh granules as employed in Example 1.

The absorption stage was as conducted in Example 1.

Regeneration was performed by passing air, heated to 70° C. and thereafter saturated with water, down through the bed of absorbent for 2.3 hours.

After regeneration, the bed of absorbent was dried to constant weight and allowed to cool to the absorption temperature before flow of the test gas was recommenced.

The total time during which the bed of absorbent was absorbing sulphur from the test gas, without breakthrough occurring, was 5.7 hours and the sulphur content of the absorbent down the bed, on termination of the experiment, was as follows:

| Bed Portion | Sulphur Content (% w/w) |
|---|---|
| A | 13.4 |
| B | 13.4 |
| C | 12.1 |
| D | 8.4 |
| E | 5.3 |
| F | 1.0 |
| Average | 8.9 |

Thus a bed of zinc oxide-containing absorbent after one regeneration using a gas stream saturated at 70° C. can retain about more sulphur than the "dry" gas regenerated absorbent of Example 1.

EXAMPLE 7

In this example the effect of regeneration by a water-containing liquid at higher temperatures is shown.

The absorbent employed was a sample of fresh granules as employed in Example 1.

The absorption stage was as conducted in Example 1.

The regeneration was conducted in a similar manner to that of Example 4. Sufficient liquid water, at 70° C., was added to the bed of absorbent so as to fill the pores of the absorbent with water. The bed of absorbent was then left at 70° C., without flow of gas or liquid therethrough, for 4 hours. The bed of absorbent was then dried out for 132 hours to a constant weight by passing "dry" nitrogen through the bed. Most of the water was in fact lost in the first 24 hours of the drying stage. The bed of absorbent was allowed to cool to the initial absorption temperature, whereupon flow of the test gas was again recommenced and the experiment was terminated on subsequent breakthrough.

The total time during which the bed of absorbent was absorbing sulphur from the test gas, without breakthrough occurring, was 7.1 hours and the sulphur content of the absorbent down the bed, on termination of the experiment, was as follows:

| Bed Portion | Sulphur Content (% w/w) |
|---|---|
| A | 13.9 |
| B | 14.1 |
| C | 13.0 |
| D | 10.1 |
| E | 5.9 |
| F | 1.0 |
| Average | 9.7 |

Thus a bed of zinc oxide-containing absorbent after one regeneration using a water-containing liquid can retain about 33% more sulphur than the "dry" gas regenerated absorbent of Example 1.

EXAMPLE 8

In this example the effect is shown of regenerating the absorbent using a water-containing gas stream, having a relative humidity of 50%.

The absorbent employed was a sample of fresh granules as employed in Example 1.

The absorption stage was as conducted in Example 1.

Regeneration was performed by using hydrogen sulphide-free methane, in admixture with sufficient water so as to be 50% saturated with water at 20° C. The "semi-wet" methane was passed down the bed of absorbent at about 20° C. and atmospheric pressure at a space velocity twice that previously used, i.e. 1400 hr$^{-1}$, for 104 hours. Thus the same amount of water was contacted each hour as when fully saturated methane is employed at a space velocity of 700 hr$^{-1}$.

A drying stage was then performed after the regeneration stage, wherein "dry" hydrogen sulphide-free methane was passed down the bed for 100 hours at the a space velocity of 700 hr$^{-1}$.

| Bed Portion | Sulphur Content (% w/w) |
|---|---|
| A | 11.2 |
| B | 11.7 |
| C | 11.1 |
| D | 8.9 |
| E | 5.5 |
| F | 1.6 |
| Average | 8.3 |

Thus a bed of zinc oxide-containing absorbent after one regeneration using a gas half saturated with water can retain about 14% more sulphur than the "dry" gas regenerated absorbent of Example 1.

We claim:

1. A process for the removal of hydrogen sulphide from a substantially water-free hydrogen sulphide-containing feedstock stream comprising passing the feedstock stream, at a temperature between $-10°$ and 350° C. through a bed of zinc oxide-containing absorbent particles thereby forming a hydrogen sulphide-depleted product stream and in order to increase the absorption capacity of the particles for hydrogen sulphide, after a period of use for absorption of hydrogen sulphide from the feedstock stream contacting the particles with a water-containing fluid so as to temporarily increase the water content within the fluid space of the bed for a period of time until the particles absorb such an amount of water that the particles increase in weight by an amount in the range 0.5 to 20%.

2. A process according to claim 1 wherein said particles when contacted with said water-containing fluid absorb water so as to increase in weight by an amount equivalent to at least 0.2 mg per m$^2$ of the surface area of said particles, as measured prior to the contacting of said feedstock stream with said particles.

3. A process according to claim 1 wherein said water-containing fluid is contacted with said particles whilst said particles are not reacting with the hydrogen sulphide in said feedstock stream.

4. A process according to claim 3 wherein at least two beds of said particles, and while a bed of said particles is reacting with the hydrogen sulphide in said feedstock stream, another bed of said particles is contacted with said water-containing fluid.

5. A process according to claim 1 wherein said particles are contacted with the water-containing fluid by passing said water-containing fluid through said bed of said particles.

6. A process according to claim 1 wherein said particles in said bed are contacted with said water-containing fluid by introducing a quantity of said water-containing fluid into said bed, the amount of water in said quantity of said water-containing fluid being at least sufficient to increase the weight of said particles by an amount in the range 0.5 to 2.0%, and holding said quantity of said water-containing fluid within said bed for a period of time sufficient for said particles to absorb an amount of water so as to increase in weight by an amount in the range 0.5 to 2.0%.

7. A process according to claim 5 wherein said water-containing fluid is a feedstock stream to which water is added for the period of time during which said particles absorb water from said water-containing stream.

8. A process according to claim 1 wherein said water-containing fluid comprises part of said product stream to which water has been added.

9. A process according to claim 8 wherein after contacting said water-containing fluid with said particles said water-containing fluid is combined with said product stream.

10. A process according to claim 9 wherein after contacting said water-containing fluid with said particles said water-containing fluid is dried, before or after combination thereof with said product stream.

* * * * *